United States Patent [19]
Lindstrom

[11] Patent Number: 5,628,794
[45] Date of Patent: May 13, 1997

[54] MULTIFOCAL CORNEAL IMPLANT LENS HAVING A HYDROGELO COATING

[76] Inventor: Richard L. Lindstrom, 2811 Westwood Rd., Wayzata, Minn. 55391

[21] Appl. No.: 613,958

[22] Filed: Mar. 8, 1996

[51] Int. Cl.⁶ .................................................. A61F 2/14
[52] U.S. Cl. .................................. 623/5; 427/2.24
[58] Field of Search ................ 623/4, 5, 6; 427/2.24; 351/160

[56] References Cited

U.S. PATENT DOCUMENTS

| | | | |
|---|---|---|---|
| 4,166,255 | 8/1979 | Graham | 351/160 |
| 4,624,669 | 11/1986 | Grendahl | 623/5 |
| 4,799,931 | 1/1989 | Lindstrom | 623/5 |
| 4,994,080 | 2/1991 | Shepard | 623/5 |
| 5,030,230 | 7/1991 | White | 623/5 |
| 5,336,261 | 8/1994 | Barrett et al. | 623/5 |

*Primary Examiner*—Randy C. Shay
*Attorney, Agent, or Firm*—Hugh D. Jaeger

[57] ABSTRACT

Hydrogel coated multifocal intraocular implantable lens having an anti-glare edge surrounded by a hydrogel ring having nutrient passage capabilities.

18 Claims, 8 Drawing Sheets

MULTIFOCAL CORNEAL IMPLANT LENS HAVING A HYDROGELO COATING

CROSS REFERENCES TO CO-PENDING APPLICATIONS

None.

BACKGROUND OF THE INVENTION

1. Field of the Invention

The present invention is for an intraocular lens, and more particularly, pertains to a small corneal implant lens which provides multifocal capability for the correction of presbyopia or ametropia and is coated with a hydrogel material for improved transmission of nutrients and reduced irritation of the tissue surrounding the implant.

The invention relates specifically to a corneal implant lens which is substantially smaller than the pupil and is coated with a hydrogel material. In the preferred form, the lens is annular in shape and the central hole is filled with a hydrogel material. The inner and outer circumferences have anti-glare edges. The outer edge is covered with a hydrogel material which serves to increase the physical diameter of the lens to improve the fixation characteristics by reducing the irritation normally caused by edges and to reduce the tendency of an otherwise small lens to be displaced by casual rubbing of the eye by the user.

2. Description of the Prior Art

Various annular corneal implant lens designs exist in the prior art. Some configurations have two or more discrete lens areas which serve to bring the impinging rays from an object to a sharp focus on a portion of the retina serviced by the lens area having a focal length closest to the optimum for the object distance. The use of smaller corneal implant lenses has also been suggested in the prior art.

While corneal implant lenses have been found to offer significant advantages over other methods of correcting certain vision defects, the implants introduce their own set of problems. For example, the cornea is living tissue and must continue to receive nutrients. This has led to the development of lenses with holes to accommodate the passage of nutrient carrying liquids. It has also led to the investigation of smaller lenses, which, because of their small size, offer less of an impediment to the transfer of liquids than other, larger lenses. While reducing the size of the lens provides an advantageous improvement in the nutrient flow, the smaller lenses are more likely to be displaced from their initial implant position by such actions as the patient rubbing the eyes containing the lens. The lamellae of the corneal tissue are oriented in planes which are generally parallel to the surface. Since the corneal implant lens is oriented in the same plane, there is little impediment to movement along the plane, between the lamellae layers. The unconscious nature of rubbing the eye makes it virtually impossible to prevent the wearer from occasionally touching the eye and potentially displacing the lens. Fixation techniques used with lenses positioned in the capsular bag of a removed natural lens are not applicable to corneal implants.

The existing devices and surgical implant techniques do not provide a satisfactory solution to the fixation problem. This is one of the reasons that the small corneal implant lenses have not found wide use.

Another problem, also related to the physical anatomical structure of the corneal lamellae, is the irritation caused by the edges of the implant lens. It is unfortunate that the edge geometry which causes the least irritation generates annoying secondary images due to diffraction and reflection. The edge geometry which has been found to substantially reduce secondary images is unacceptable from the standpoint of tissue irritation and the attendant complications that such irritation causes.

Of course, there is the need for a multifocal lens which can correct for the loss of accommodation which accompanies aging. One technique is to form the lens with a centrally positioned hole, which has no correction, allowing the eye to focus two images on the retina. While this technique provides substantial advantages, the interior edge generates further unwanted secondary images by diffraction and reflection.

What is needed is a small corneal implant lens which does not provide a substantial impediment to the natural flow of nutrients in the cornea but is nevertheless not prone to accidental displacement by casual rubbing of the eye, which does not irritate the corneal tissue and does not have secondary images caused by edge diffraction. Even further, the lens should provide multifocal capability. Quite unfortunately, the requirements for nutrient flow are such that they contradict the requirements for good fixation, while the larger lenses that provide better fixation do not allow adequate nutrient flow. Similarly, the reduction of edge diffraction effects has been accomplished at the expense of increased tissue irritation. Or, conversely, the reduction of tissue irritation has been achieved with techniques that increase the secondary image problem.

The multifocal corneal implant lens of this invention is quite small in size, but, because of the hydrogel extension about the periphery, is not easily displaced by casual rubbing of the eye. Holes in the lens which allow the passage of nutrients are filled with hydrogel which allows the flow of nutrients but prevents the hole from being filled with scar tissue. The hydrogel coating significantly improves the compatibility of the lens to the living tissue of the cornea and also serves to reduce the irritation otherwise caused by non-glare edges of the lens. The effectiveness of the non-glare edges is further improved by the hydrogel coating, which has an index of refraction intermediate between the lens and the tissue of the cornea.

SUMMARY OF THE INVENTION

The general purpose of the present invention is a multifocal corneal implant lens having a hydrogel coating.

According to one embodiment of the present invention, there is provided a corneal implant lens fabricated from a suitable material such as PMMA (polymethylmethacrylate), polysulfone or polycarbonate. The lens may be circular or annular in shape and may contain a plurality of holes for the passage of nutrients. The outer edge, and in the case of the annular lens, the inner edge as well, are configured to reduce the effect of diffraction and the attendant secondary images. The entire lens is coated with a hydrogel material which fills the nutrient passage holes, and in the case of the annular lens, the central hole as well. Ideally, the hydrogel material extends well beyond the outer periphery of the lens to increase the effective diameter.

One significant aspect and feature of the present invention is a small, multifocal corneal implant lens which has improved bio-compatibility over PMMA, polysulfone, polycarbonate and the like materials and is less prone to displacement by casual rubbing of the eye.

Another significant aspect and feature of the present invention is a corneal implant lens having nutrient transmission holes therein which are filled with permeable hydrogel material which prevents the growth of scar tissue within the holes.

Still another significant aspect and feature of the present invention is a corneal implant lens of PMMA, polysulfone, polycarbonate or the like material having edges configured to reduce the secondary images caused by edge diffraction where the edges are coated with a hydrogel material having an index of refraction intermediate the index of refraction of the lens and the index of refraction of the corneal tissue.

Having thus described embodiments of the present invention, it is the principal object of the present invention to provide a multifocal corneal lens having a hydrogel coating.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
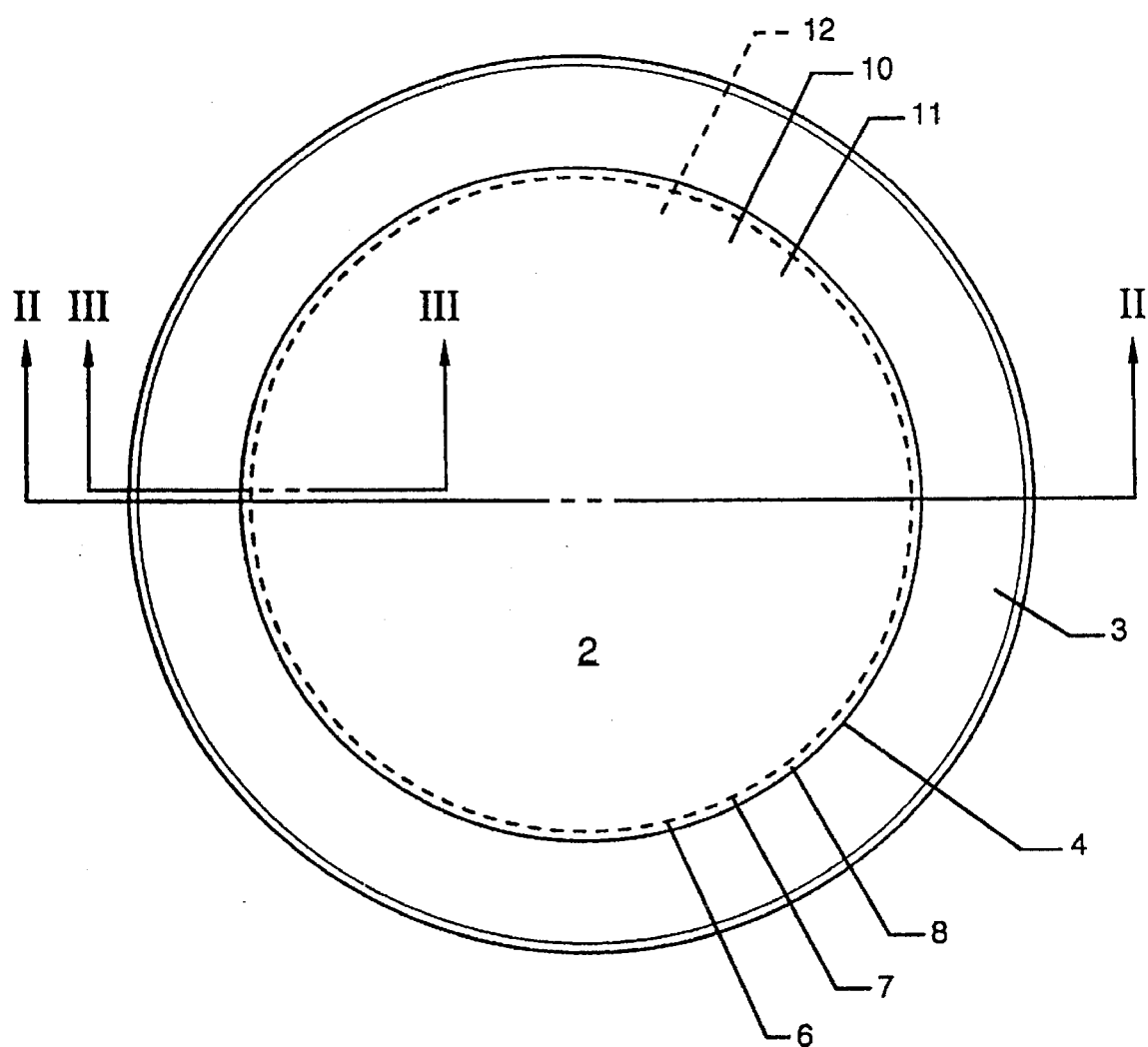
FIG. 1 illustrates a front view of a small corneal implant lens according to the invention.
Figure 2:
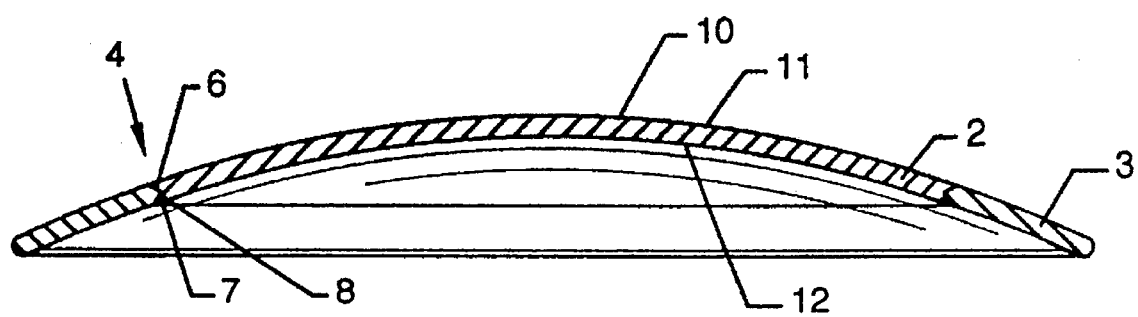
FIG. 2 illustrates a cross-sectional view along the line II—II of FIG. 1.

FIG. 1 illustrates a corneal implant lens 2, of rigid bio-compatible material such as polysulfone, polycarbonate or PMMA, is fabricated using conventional techniques. About the periphery of lens 2, and affixed thereto, is a ring 3 of flexible hydrogel material. As shown in FIG. 2, hydrogel ring 3 is the same thickness as lens 2 and conforms to the same general shape. It can also be seen from FIG. 2 that the edge 4 of lens 2 is completely encapsulated by hydrogel ring 3. Edge 4 may have a geometry which reduces the effect of edge diffraction as shown. It will be observed that the geometry of edge 4 provides a sharp upper edge 6 and a sharp lower edge 7, with a connecting V-groove 8 which extends completely around lens 2. The sharp edges 6 and 7 would ordinarily constitute a source of irritation to the corneal tissue if the lens were implanted without the protection of hydrogel ring 3.

The shape of hydrogel ring 3 conforms generally to the shape of lens 2 although it may differ slightly depending on the optical effect which is desired. Typically, the hydrogel ring 3 serves simply as a mechanical device to improve the stability of lens 2 when it is implanted in the cornea and as a protective cover for the anti-diffraction geometric treatment of edge 4. In such cases, the curvature of hydrogel ring 3 will be such that there is little or no alteration of the point at which light rays passing through are brought to a focus.

The hydrogel ring 3 serves as a physical buffer for the sharp edges 6 and 7 and thereby permits the reduction of the secondary diffraction image by accommodating the utilization of an edge treatment which would otherwise be impossible for a corneal implant lens. The hydrogel ring 3 provides a further beneficial diffraction reducing effect by serving as an intermediate medium between the material of lens 2 and the corneal tissue. The index of refraction of material typically used for lens 2 is in the range of 1.55 to 1.50. The corneal tissue has an index of refraction which approximates 1.376. Since the diffraction effects are enhanced by indices of refraction which are far apart and reduced by indices which are closer together, the index of refraction for hydrogel ring 3 is selected to lie between the values for lens 2 and the corneal tissue. Typical values for the index of refraction of hydrogel ring 3 lie in the range of 1.40 to 1.45.

The lens 2 has a thin coating of hydrogel material over the entire anterior surface 11 and the entire posterior surface 12. The thickness of this coating may lie in the range of 0.001 to 100 microns. The purpose of the hydrogel coating is to improve the bio-compatibility and deter the otherwise bothersome giant cell reaction as the body attempts to sequester the foreign material. Hydrogels are less prone to this type of reaction.

While the optical shape of hydrogel ring 3 is preferably such that it does not modify the focal point of the rays passing through, it will be appreciated that the shape can be configured to provide multifocal capability, if desired.

Figure 3:
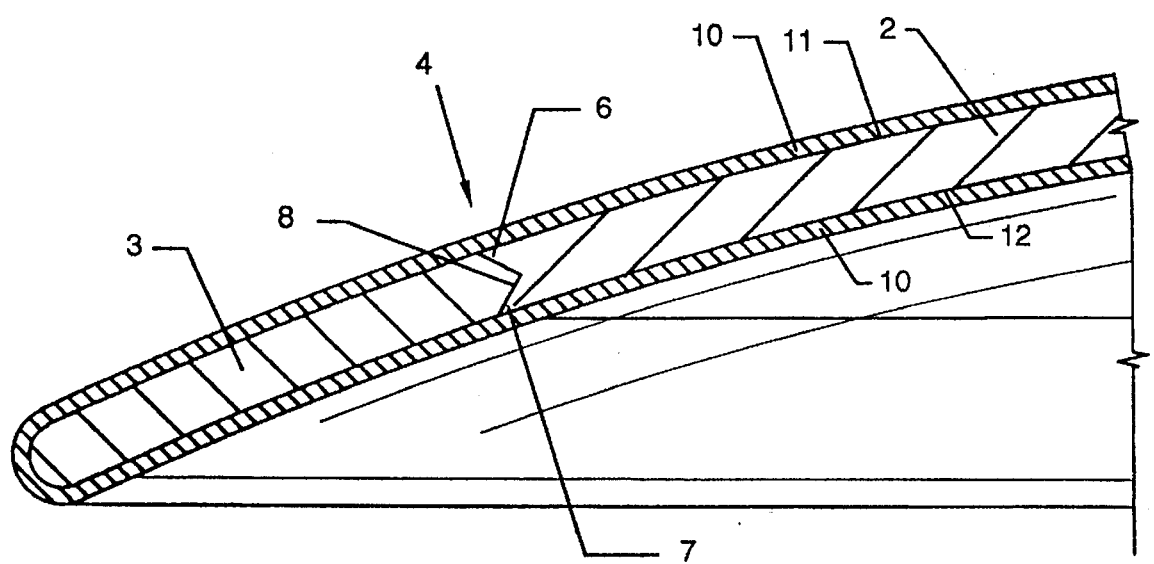
FIG. 3 illustrates a conceptual cross-sectional view along line III—III of FIG. 1.

FIG. 3 is a conceptual cross-sectional view along line III—III of FIG. 1 where all numerals correspond to those elements previously described. Illustrated in particular is the junction of the edge 4 and the hydrogel ring 3. It is also observed that the hydrogel material 10 is contiguous with the hydrogel ring 3, the anterior surface 11, and the posterior surface 12, to provide a continuous homogenous coating about the entire lens 2.

Figure 4:
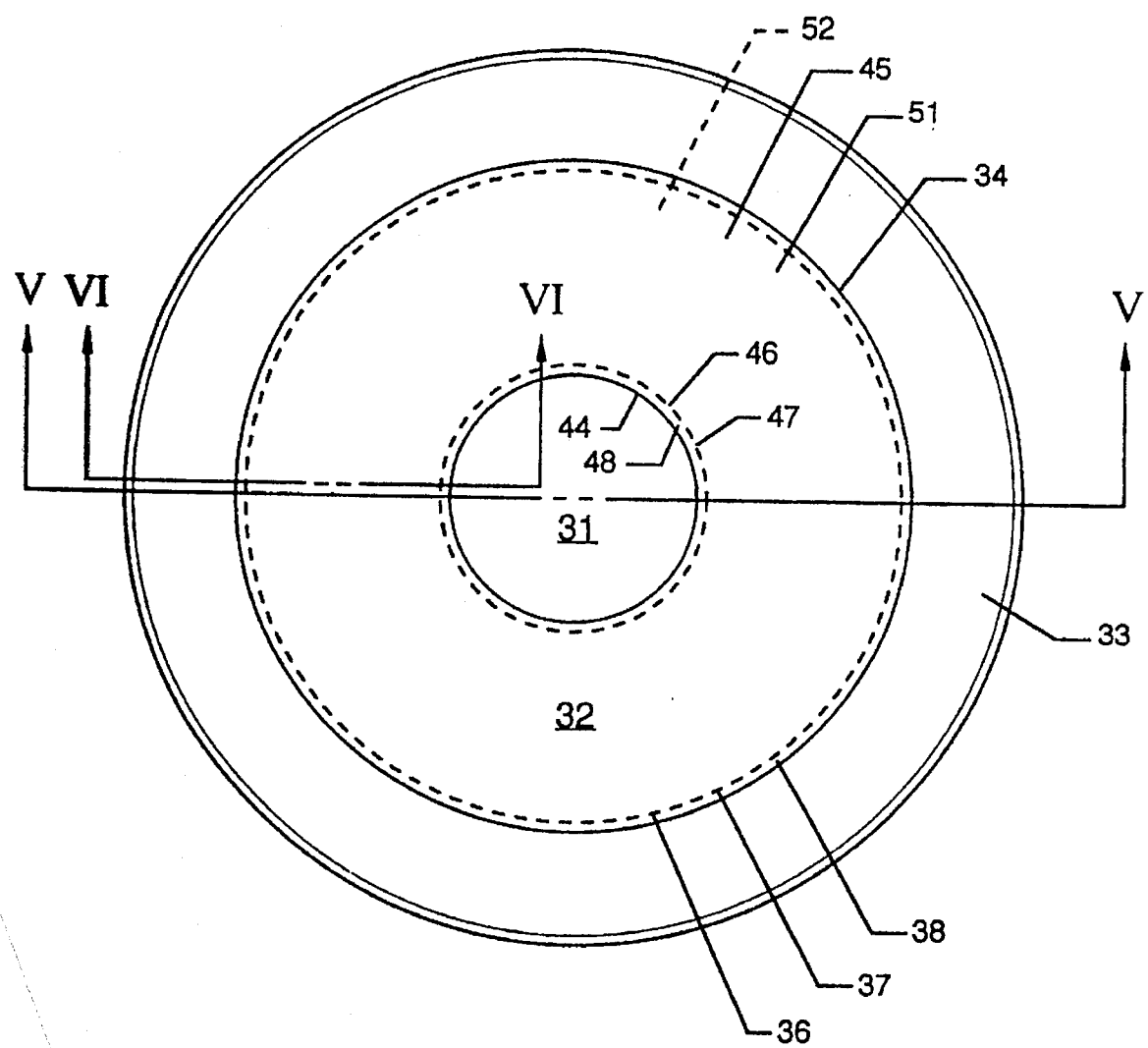
FIG. 4 illustrates a front view of a small corneal implant lens having an axially centered hole.
Figure 5:
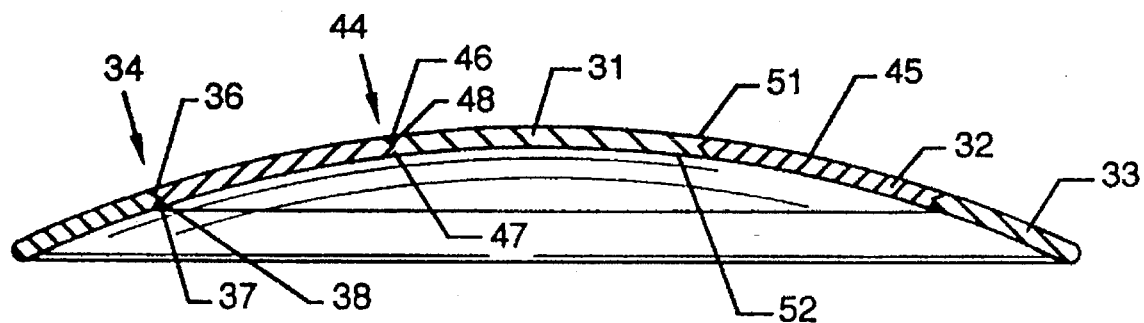
FIG. 5 illustrates a cross-sectional view along the line IV—IV of FIG. 4.
Figure 6:
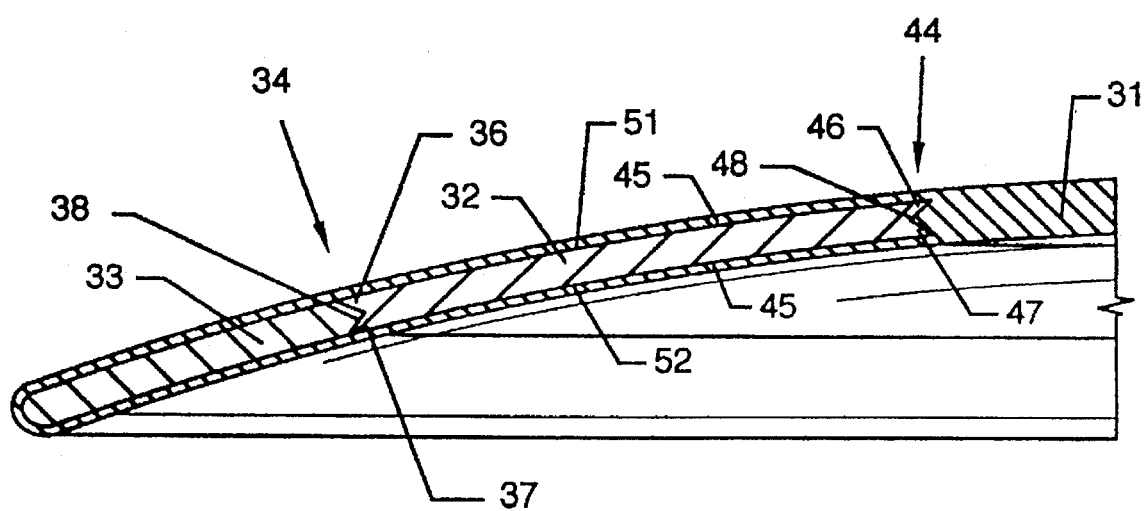
FIG. 6 illustrates a conceptual cross-sectional view along line VI—VI of FIG. 4.

FIG. 4 illustrates a corneal implant lens 32 of rigid bio-compatible material, such as polysulfone, polycarbonate or PMMA, fabricated using conventional techniques. Lens 32 has an axially centered hole 31. The diameter of lens 32 is selected to be less than 2.5 mm and the diameter of hole 31 is within the range of 100 microns to 0.1 mm. In the same fashion as with respect to the embodiment of FIG. 1, a ring 33 of flexible hydrogel material is affixed to the periphery of lens 32. As shown in FIGS. 5 and 6, the outer edge 34 of lens 32 has a geometric shape which minimizes the diffracted image as well as the image reflected from the edge 34. The geometric shape includes a sharp upper edge 36 and a sharp lower edge 37, with a connecting V-groove 38 which extends completely around the periphery of lens 32.

The inner edge 44 has an edge treatment similar to that of outer edge 34, including a sharp upper edge 46 and a sharp lower edge 47, with a connecting V-groove 48 extending completely abound the periphery of lens 32. This shape minimizes the diffracted and reflected image from the inner edge 44. The hole 31 is filled in a contiguous fashion with hydrogel material 45, which may be the same material as that of ring 33 and of the hydrogel coating. The physical shape and index of refraction of the hydrogel material in hole 31 may be selected so as not to modify the point of focus of the rays passing through. In this case, the other optical elements between the object and the retina will determine the point of focus. This would be advantageous when the patient is suffered from presbyopia and the lens 32 provides the necessary correction for close objects, allowing far objects to be viewed through hole 31 without correction.

Alternatively, the shape and the index of refraction of the hydrogel in hole 31 may be selected to provide modification of the point of focus of the rays passing through.

In the fashion of the hydrogel ring 3, described with reference to the embodiment of FIG. 1, the shape of hydrogel ring 33 conforms generally to the shape of lens 32 although it may differ slightly depending on the optical effect which is desired. Typically, the hydrogel ring 33 serves simply as a mechanical device to improve the stability of lens 32 when it is implanted in the cornea and as a protective cover for the anti-diffraction geometric treatment of edge 34. In such cases, the curvature of hydrogel ring 33 will be such that there is little or no alteration of the point at which light rays passing through are brought to a focus.

The hydrogel ring 33 serves as a physical buffer for the sharp edges 36 and 37 and thereby permits the reduction of the secondary diffraction image by accommodating the utilization of an edge treatment which would otherwise be impossible for a corneal implant lens. In like fashion, the hydrogel coating 45, which also serves as a filler in hole 31 protects the corneal implant tissue from the sharp edges 46 and 47. The hydrogel filler in hole 31 and hydrogel ring 33 provide a further beneficial diffraction reducing effect by serving as an intermediate medium between the material of lens 32 and the corneal tissue. The index of refraction of material typically used for lens 32 is in the range of 1.55 to 1.50. The corneal tissue has an index of refraction which approximates 1.376. Since the diffraction effects are enhanced by indices of refraction which are far apart and reduced by indices which are closer together, the index of refraction for hydrogel ring 33 and the hydrogel filler in hole 31 is selected to lie between the values for lens 32 and the corneal tissue. Typical values for the index of refraction of hydrogel used in the embodiment of FIGS. 4 and 5 lie in the range of 1.40 to 1.45.

The lens 32 has a thin coating of hydrogel material 45 over the entire anterior surface 51 and the entire posterior surface 52. The thickness of this coating may lie in the range of 0.001 to 100 microns. The purpose of the hydrogel coating is to improve the bio-compatibility and deter the otherwise bothersome giant cell reaction as the body attempts to sequester the foreign material. Hydrogels are less prone to this type of reaction.

FIG. 5 is a cross-sectional view along line V—V of FIG. 4 where all numerals correspond to those elements previously described.

FIG. 6 is a cross-sectional view along line VI—VI of FIG. 4 where all numerals correspond to those elements previously described. Illustrated in particular is the junction of the edge 34 with the hydrogel ring 33 and the junction of the edge 44 with the hole 31. It is also observed that the hydrogel material 45 is contiguous with the hydrogel ring 33, the hole 31, the anterior surface 51, and the posterior surface 52, to provide a continuous homogenous coating about the entire lens 32.

Figure 7:
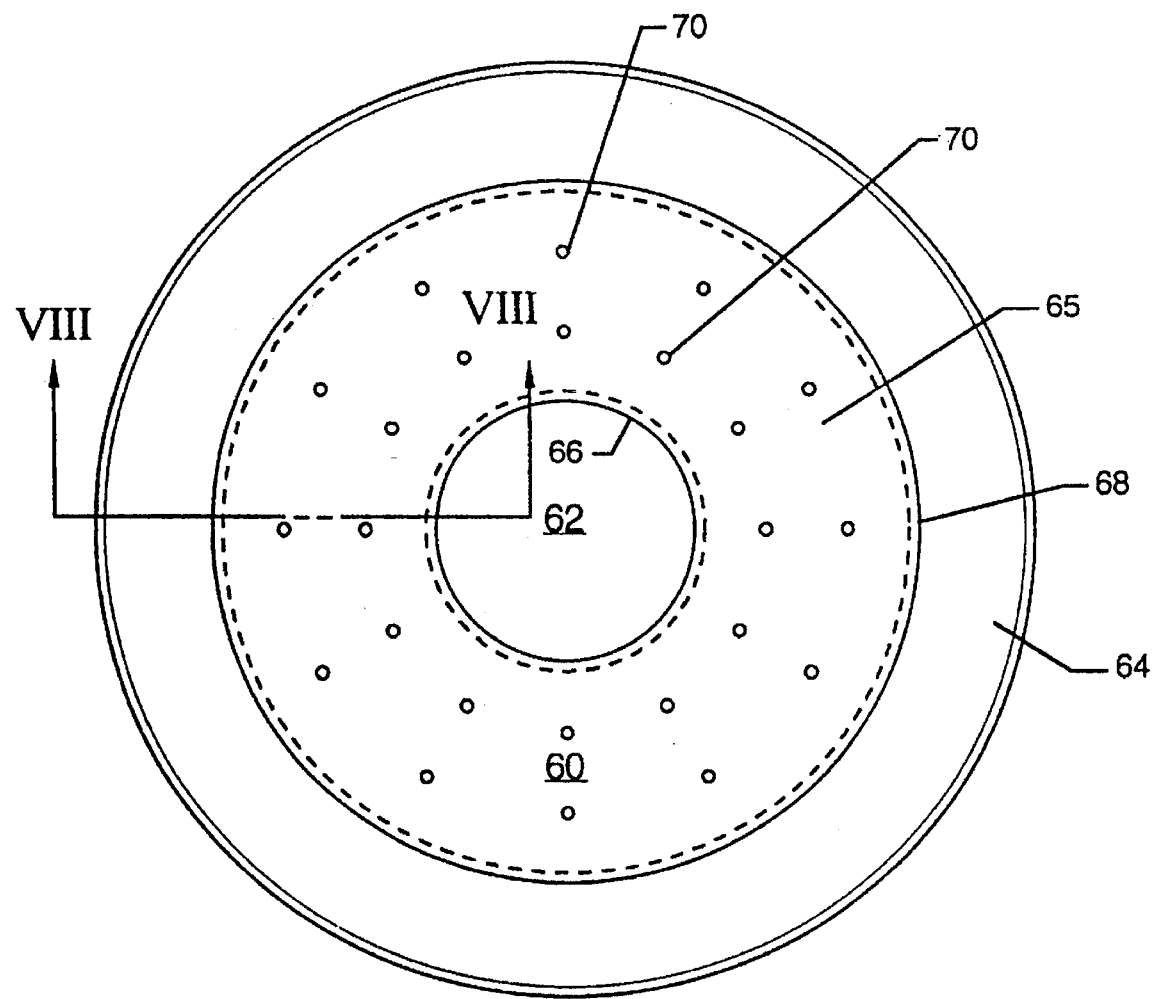
FIG. 7 illustrates a front view of a small corneal implant lens having an axially positioned hole and a plurality of holes for nutrient passage; and, FIG. 8 illustrates a cross-sectional view along line VIII—VIII of FIG. 7.

The embodiment shown in FIG. 7 includes a small corneal implant lens 60 of rigid bio-compatible material, such as polysulfone, polycarbonate or PMMA, having a diameter less than 2.5 mm. A hole 62 in the center of lens 60 has a diameter in the range of 100 microns to 0.1 mm. In the same fashion as the previously described embodiments, a ring 64 of hydrogel material 65 is affixed to the periphery of lens 60. The treatment of the inner edge 66 and outer edge 68 is similar to that of the previously described embodiments.

A plurality of small holes 70 which may range from 0.000001 mm to 1.0 mm in diameter are arranged about or near the periphery of lens 60 or, alternatively, may be located closer to the center of lens 60. These holes 70 facilitate the passage of nutrients to the corneal tissue overlaying the implant lens.

Such holes commonly become filled with scar tissue in the form of giant cells, which eventually block the flow of nutrients through the holes. To prevent this from occurring, holes 70 are filled with hydrogel material 65 which does not block the flow of nutrients but prevents the incursion of scar tissue and thereby preserves the flow of nutrients through the lens.

Figure 8:
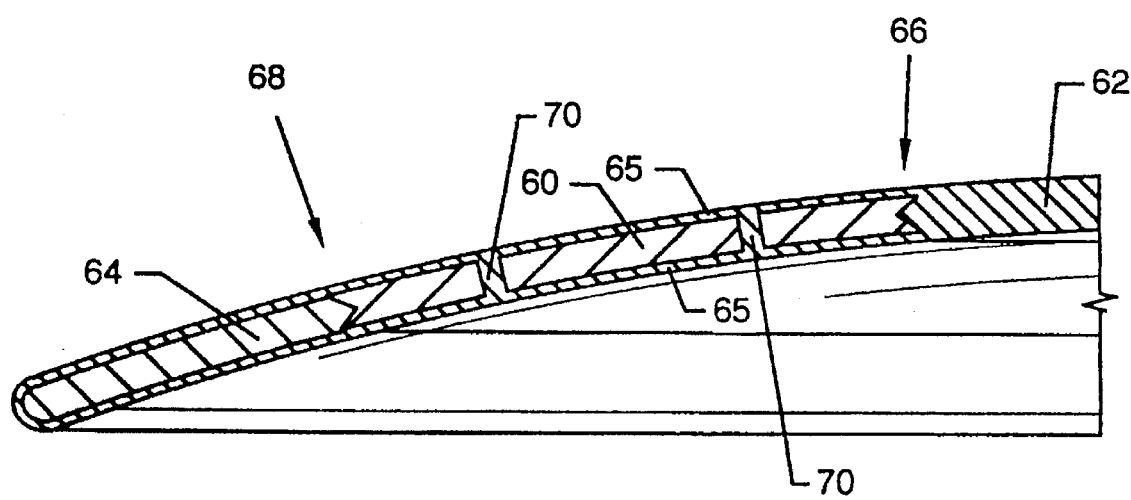

FIG. 8 is a cross-sectional view along line VIII—VIII of FIG. 7 where all numerals correspond to those elements previously described.

Various modifications can be made to the present invention without departing from the apparent scope hereof.

I claim:

1. A small corneal implant lens of rigid material having an outer diameter less than 2.5 mm and having an outer edge;
   a. said lens having a coating of hydrogel material in the range from 0.001 to 100 microns thick over an active area of said lens;
   b. said lens including a ring of hydrogel material extending outwardly from said outer edge of said lens at least 0.5 mm;
   c. wherein the outer edge of said lens has a geometric shape selected for the minimization of the diffracted image from said edge.

2. A small corneal implant lens of rigid material having an outer diameter less than 2.5 mm and having an outer edge;
   a. said lens having a coating of hydrogel material in the range from 0.001 to 100 microns thick over an active area of said lens;
   b. said lens including a ring of hydrogel material extending outwardly from said outer edge of said lens at least 0.5 mm;
   c. wherein the outer edge of said lens has a geometric shape selected for the minimization of the reflected image from said edge.

3. A small corneal implant lens according to claim 1, wherein the outer edge of said lens has a geometric shape selected for the minimization of the diffracted and reflected images from said edge.

4. A small corneal implant lens according to claim 1, wherein said rigid material is selected from the group of polysulfone, PMMA, and polycarbonates.

5. A small corneal implant lens according to claim 1, wherein said hydrogel coating has an index of refraction intermediate the index of refraction of said rigid material and the index of refraction of corneal tissue.

6. A small corneal implant lens according to claim 1, wherein said lens has at least one hole therein and said hydrogel coating fills said hole.

7. A small corneal implant lens according to claim 1, wherein said lens has a plurality of holes therein and said hydrogel coating fills said holes.

8. A small corneal implant lens according to claim 1, wherein said lens has an axially centered hole having a diameter in the range of 100 microns to 0.1 mm and said hydrogel coating fills said hole.

9. A small corneal implant lens according to claim 1, wherein said lens has an axially centered hole having a diameter sufficient to generate a readily usable image of an object at a different distance than the distance of the object providing a readily usable image when viewed through said lens.

10. A small corneal implant lens according to claim 9, wherein said lens has a plurality of holes therein and said hydrogel coating fills said holes.

11. A small corneal implant lens according to claim 10, wherein a plurality of said holes have a diameter in the range of 0.000001 mm to 1.0 mm.

12. A small corneal implant lens according to claim 9, wherein said axially centered hole is filled with hydrogel material having a shape and index of refraction to generate a readily usable image of an object at a different distance than the distance of the object providing a readily usable image when viewed through said lens.

13. A small corneal implant lens of rigid material having an outer diameter less than 2.5 mm and an outer edge;
  a. said lens having a ring of hydrogel material extending outwardly from said outer edge of said lens at least 0.5 mm;
  b. wherein the outer edge of said lens has a geometric shape selected for the minimization of the diffracted image from said lens.

14. A small corneal implant lens of rigid material having an outer diameter less than 2.5 mm and an outer edge;
  a. said lens having a ring of hydrogel material extending outwardly from said outer edge of said lens at least 0.5 mm;
  b. wherein the outer edge of said lens has a geometric shape selected for the minimization of the reflected image from said lens.

15. A small corneal implant lens according to claim 13, wherein the outer edge of said lens has a geometric shape selected for the minimization of the reflected and diffracted images from said edge.

16. A small corneal implant lens according to claim 13, wherein said hydrogel ring has an index of refraction intermediate the index of refraction of said rigid material and the index of refraction of corneal tissue.

17. A small corneal implant lens according to claim 14, wherein said hydrogel ring has an index of refraction intermediate the index of refraction of said rigid material and the index of refraction of corneal tissue.

18. A small corneal implant lens according to claim 15, wherein said hydrogel ring has an index of refraction intermediate the index of refraction of said rigid material and the index of refraction of corneal tissue.

* * * * *

UNITED STATES PATENT AND TRADEMARK OFFICE
CERTIFICATE OF CORRECTION

PATENT NO. : 5,628,794  
DATED : May 13, 1997  
INVENTOR(S) : Richard L. Lindstrom It is certified that error appears in the above-identified patent and that said Letters Patent is hereby corrected as shown below:

Title page,
Item [54], Title, should read
-- MULTIFOCAL CORNEAL IMPLANT LENS HAVING A HYDROGEL COATING --

Signed and Sealed this

Twenty-first Day of September, 2004

JON W. DUDAS  
*Director of the United States Patent and Trademark Office*